United States Patent
Bhullar et al.

(10) Patent No.: US 6,866,758 B2
(45) Date of Patent: Mar. 15, 2005

(54) BIOSENSOR

(75) Inventors: Raghbir S. Bhullar, Indianapolis, IN (US); Brian S. Hill, Avon, IN (US); John T. Austera, Indianapolis, IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 377 days.

(21) Appl. No.: 10/103,027

(22) Filed: Mar. 21, 2002

(65) Prior Publication Data

US 2003/0178302 A1 Sep. 25, 2003

(51) Int. Cl.[7] ............... G01N 27/327; G01N 27/333
(52) U.S. Cl. ............... 204/403.02; 204/403.01; 204/403.14; 204/416
(58) Field of Search ............ 204/403.01–403.14, 204/404, 405, 416–418

(56) References Cited

U.S. PATENT DOCUMENTS

| | | | |
|---|---|---|---|
| 4,131,484 A | 12/1978 | Caruso et al. ............... 134/1 |
| 4,874,500 A | 10/1989 | Madou et al. ............... 204/412 |
| 4,999,582 A | 3/1991 | Parks et al. ............... 324/438 |
| 5,104,480 A | 4/1992 | Wojnarowski et al. ...... 156/643 |
| 5,243,516 A | 9/1993 | White ............... 364/413.07 |
| 5,264,103 A * | 11/1993 | Yoshioka et al. ............ 205/778 |
| 5,288,636 A | 2/1994 | Pollmann et al. ............ 435/288 |
| 5,334,279 A | 8/1994 | Gregoire ............... 156/630 |
| 5,336,388 A | 8/1994 | Leader et al. ............... 204/406 |
| 5,390,412 A | 2/1995 | Gregoire ............... 29/848 |
| 5,391,250 A | 2/1995 | Cheney, II et al. ......... 156/268 |
| 5,413,690 A | 5/1995 | Kost et al. ............... 204/403 |
| 5,414,224 A | 5/1995 | Adasko et al. ............... 174/262 |
| 5,426,850 A | 6/1995 | Fukutomi et al. ............. 29/848 |
| 5,437,999 A | 8/1995 | Diebold et al. ............. 435/288 |
| 5,451,722 A | 9/1995 | Gregoire ............... 174/261 |
| 5,465,480 A | 11/1995 | Karl et al. ............... 29/825 |
| 5,502,396 A * | 3/1996 | Desarzens et al. ........ 204/403.02 |
| 5,512,489 A | 4/1996 | Girault et al. ............ 205/777.5 |
| 5,575,930 A | 11/1996 | Tietje-Girault et al. ....... 216/65 |
| 5,576,073 A | 11/1996 | Kickelhain ............... 427/555 |
| 5,593,739 A | 1/1997 | Kickelhain ............... 427/555 |
| 5,635,054 A | 6/1997 | Girault et al. ............ 205/775 |
| 5,739,039 A | 4/1998 | Girault et al. ............... 436/149 |
| 5,758,398 A | 6/1998 | Rijnbeek et al. ........... 29/25.42 |
| 5,762,770 A | 6/1998 | Pritchard et al. ........... 204/403 |
| 5,798,031 A | 8/1998 | Charlton et al. ............ 204/403 |
| 5,956,572 A | 9/1999 | Kidoguchi et al. ........... 438/96 |

(List continued on next page.)

FOREIGN PATENT DOCUMENTS

| | | | |
|---|---|---|---|
| EP | 0 480 703 | 4/1992 | ............ H01L/21/48 |
| EP | 0 875 754 | 11/1998 | ......... G01N/27/403 |
| JP | 56-100451 | 8/1981 | ............ H01L/21/92 |
| JP | 7-290751 | 1/1995 | ............ B41J/2/385 |
| JP | 9-260697 | 10/1997 | ............ H01L/31/04 |
| JP | 10-52780 | 2/1998 | ............ B23K/26/06 |
| JP | 10-241992 | 9/1998 | ............ H01G/4/255 |
| JP | 10-303444 | 11/1998 | ............ H01L/31/04 |
| JP | 11014582 | 1/1999 | ............ G01N/27/26 |
| JP | 11-297890 | 10/1999 | ............ H01L/23/12 |
| JP | 2000-121594 | 4/2000 | ......... G01N/27/327 |
| WO | WO 95/22881 | 8/1995 | ............ H05K/3/02 |
| WO | WO 98/49773 | 11/1998 | ............ H03H/3/08 |

*Primary Examiner*—Alex Noguerola
(74) *Attorney, Agent, or Firm*—Jill L. Woodburn

(57) ABSTRACT

A biosensor is provided in accordance with the present invention. The biosensor includes an electrode support substrate, electrodes positioned on the electrode support, each electrode including a meter-contact portion and a measurement portion, and a sensor support substrate. The sensor support substrate cooperates with the electrode support substrate to define channel in alignment with the measurement portion of the electrodes. Additionally, the sensor support substrate includes opposite ends and at least one window. The at least one window is spaced-apart from the ends and in alignment with the meter-contact portion of at least one of the electrodes.

5 Claims, 10 Drawing Sheets

U.S. PATENT DOCUMENTS

| | | |
|---|---|---|
| 5,965,001 A | 10/1999 | Chow et al. ................ 204/600 |
| 5,997,817 A | 12/1999 | Crismore et al. ............. 422/58 |
| 6,004,441 A | 12/1999 | Fujiwara et al. ............. 204/412 |
| 6,134,461 A | 10/2000 | Say et al. ................... 600/345 |
| 6,165,594 A | 12/2000 | Moh et al. .................. 428/207 |
| 6,175,752 B1 | 1/2001 | Say et al. ................... 600/345 |
| 6,258,229 B1 | 7/2001 | Winarta et al. .............. 204/403 |
| 6,287,451 B1 | 9/2001 | Winarta et al. ........... 205/777.5 |
| 6,299,757 B1 | 10/2001 | Feldman et al. ............ 205/775 |
| 6,309,526 B1 | 10/2001 | Fujiwara et al. ............ 204/403 |
| 6,338,790 B1 | 1/2002 | Feldman et al. ......... 205/777.5 |

\* cited by examiner

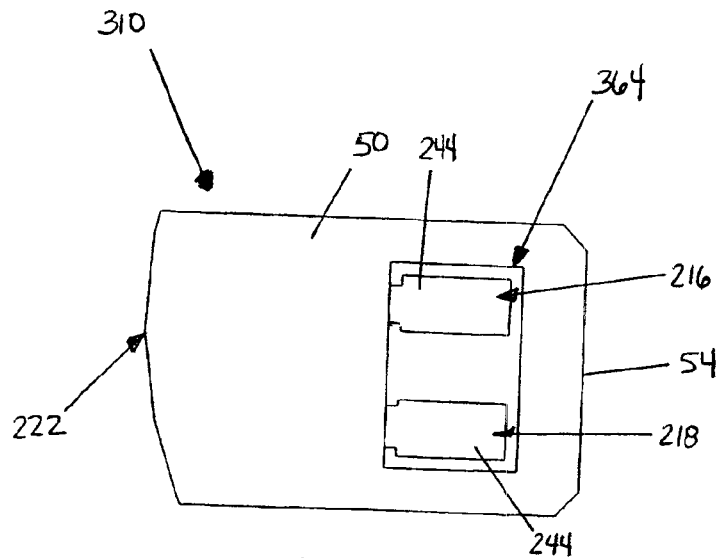
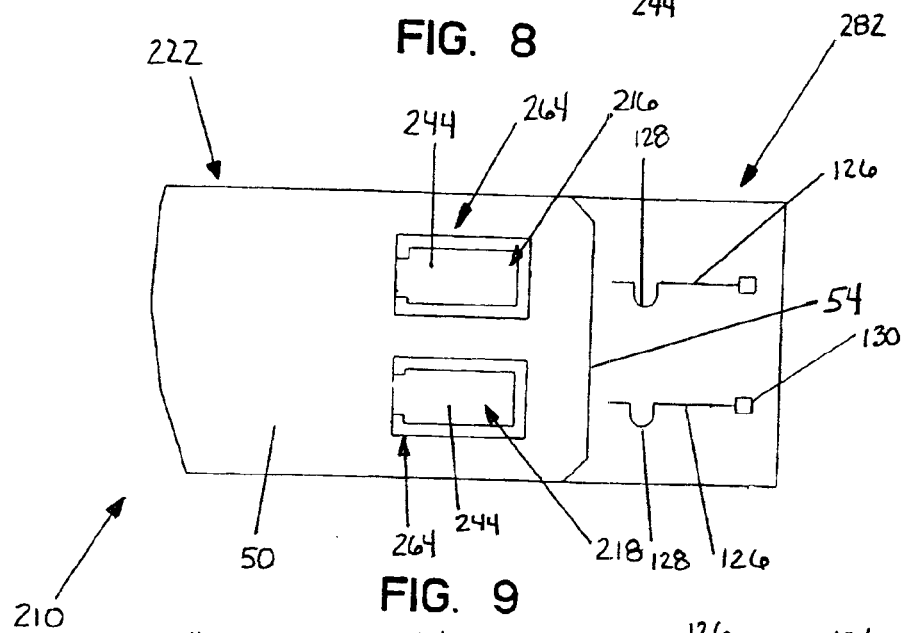
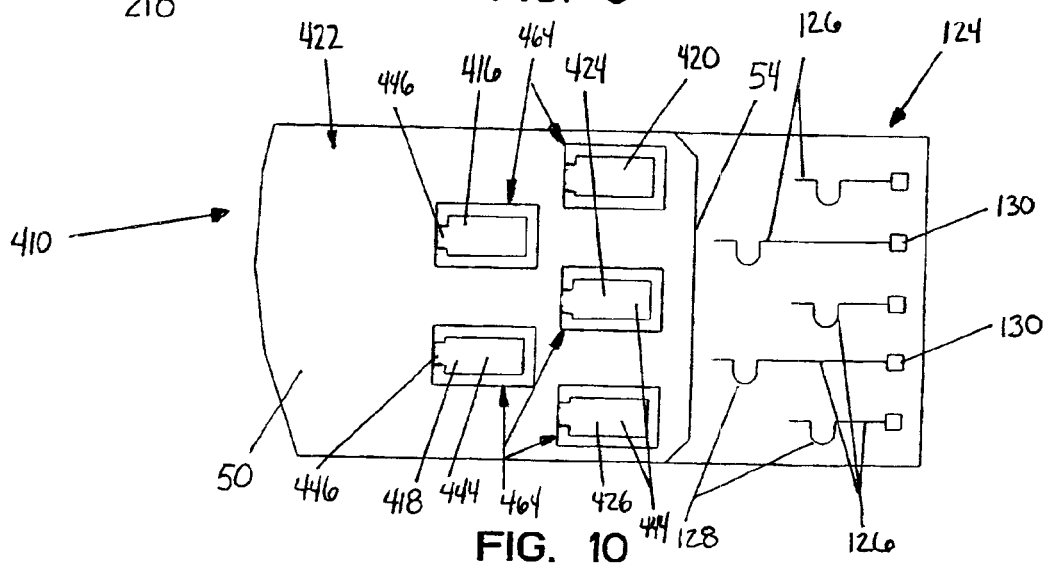

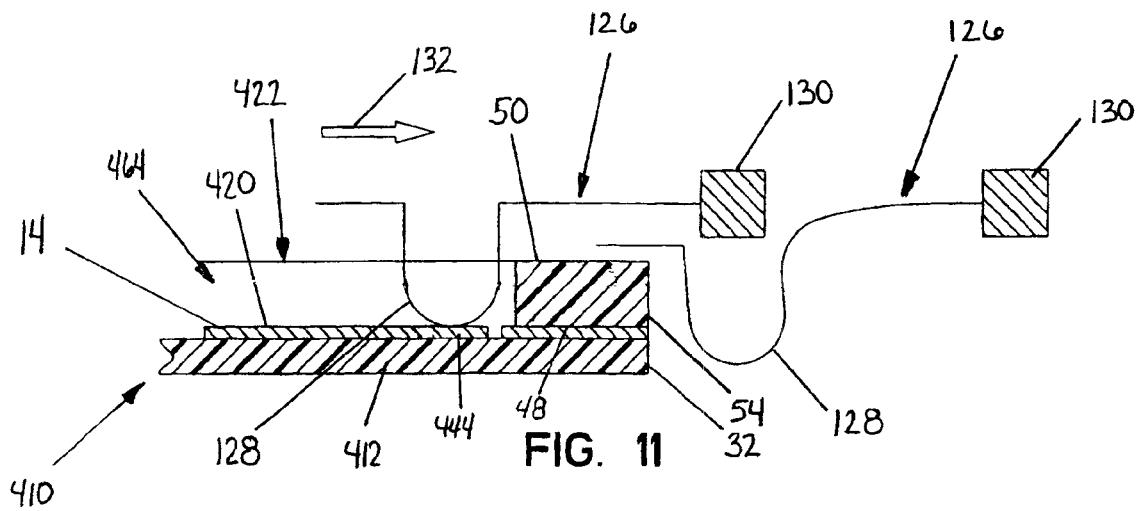
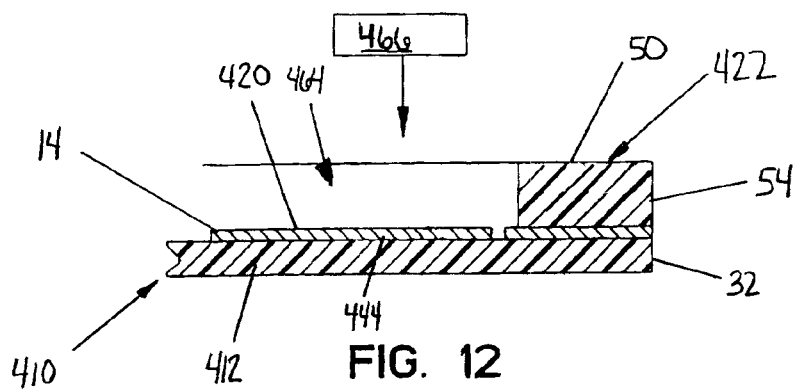
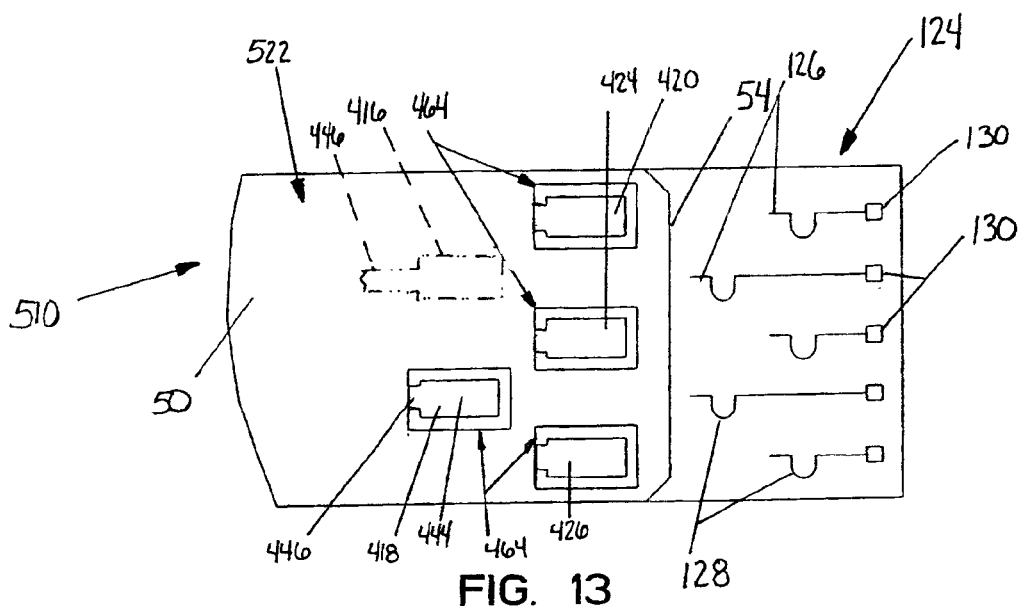

US 6,866,758 B2

BIOSENSOR

FIELD OF THE INVENTION

The present invention is directed to a biosensor and a method of forming same. More particularly, the present invention is directed to a biosensor with connector windows that expose electrode contacts for engagement with a meter.

BACKGROUND AND SUMMARY OF THE INVENTION

Electrochemical biosensors are known. They have been used to determine the concentration of various analytes from biological samples, particularly from blood. Electrochemical biosensors are described in U.S. Pat. Nos. 5,413,690; 5,762,770; 5,798,031; and 5,997,817 the disclosure of each of which is expressly incorporated herein by reference.

According to the present invention a biosensor is provided. The biosensor comprises an electrode support substrate, electrodes positioned on the electrode support, each electrode including a meter-contact portion and a measurement portion, and a sensor support substrate. The sensor support substrate cooperates with the electrode support substrate to define a channel in alignment with the measurement portion of the electrodes. Additionally, the sensor support substrate includes opposite ends and at least one window. The at least one window is spaced-apart from the ends and in alignment with the meter-contact portion of at least one of the electrodes.

According to another aspect of the invention a method of forming a biosensor is provided. The method comprises the steps of forming electrodes on a surface of an electrode support substrate, each electrode including a meter-contact portion and a measurement portion, forming a sensor support substrate having opposite ends and at least one window spaced apart from the opposite ends, coupling the sensor support and the electrode support substrate together so that the at least one window is aligned with the meter-contact portion of the electrodes, and applying a reagent to the measurement portion of the electrodes.

In accordance with another aspect of the invention a biosensor is provided. The biosensor comprises an electrode support substrate, electrodes positioned on the electrode support substrate, each electrode including a meter-contact portion and a measurement portion, a sensor support substrate coupled to the electrode support substrate, the sensor support substrate including opposite ends, an opening in alignment with the measurement portion of the electrodes and at least one window spaced-apart from the ends and in alignment with the meter-contact portion of the electrodes, and a cover coupled to the sensor support substrate.

Additional features of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which:

FIG. 8 is an enlarged top diagrammatic view of a biosensor in accordance with another aspect of the present invention showing one window exposing two electrode contacts.

FIG. 9 is an enlarged top diagrammatic view of a biosensor of FIG. 8 and a diagrammatic view of a corresponding meter showing the meter including two contacts for engagement with the two exposed electrode contacts of the biosensor.

FIG. 10 is a view similar to FIG. 8 of a biosensor in accordance with another aspect of the present invention showing five windows exposing five electrode contacts and showing a diagrammatic view of a corresponding meter including five contacts for engagement with the five exposed electrode contacts.

FIG. 11 is an enlarged cross-sectional view of one window of the biosensor of FIG. 10 and showing one meter contact sequenced in time in order to illustrate the relative positioning of the electrode contact and the meter contact during insertion of the biosensor in the meter.

FIG. 12 is an enlarged cross-sectional view of one window of the biosensor of FIG. 10 and showing a diagrammatic view of a switch in accordance with another aspect of the present invention.

FIG. 13 is a view similar to FIG. 8 of a biosensor in accordance with another aspect of the present invention showing four windows exposing four electrode contacts with one closed window in phantom and showing a diagrammatic view of a corresponding meter including five contacts.

DETAILED DESCRIPTION OF THE DRAWINGS

The present invention relates to a biosensor and method of manufacturing said biosensor. This biosensor of the present invention includes opposite ends and is beneficially formed to enable a user to grasp ends without touching electrode contacts, which are themselves formed to electrically connect with a meter. Biosensors of the present invention include at least one discrete window spaced-apart from the end of the biosensor. The at least one window serves as a built-in fiducial for alignment of the biosensor, enabling easy automated process control during assembly. Further, the at least one discrete window is a significant advantage for an integrated strip handling system, since each window creates a detent, providing mechanical feedback for strip mating with meter contacts. Furthermore, when biosensor includes discrete windows, strip alignment problems are eliminated enabling multiple strip configurations to be used with a single meter. That is, the discrete windows of the biosensor prevent problems associated with closely spaced electrode pads touching the wrong meter contact. Aspects of the invention are presented in FIGS. 1–15, which are not drawn to scale and wherein like components in the several views are numbered alike.

A biosensor 10 is shown in FIGS. 1–4. The term analyte, as used herein, refers to the molecule or compound to be quantitatively determined. Non-limiting examples of analytes include carbohydrates, proteins, such as hormones and other secreted proteins, enzymes, and cell surface proteins; glycoproteins; peptides; small molecules; polysaccharides; antibodies (including monoclonal or polyclonal Ab); nucleic acids; drugs; toxins; viruses of virus particles; portions of a cell wall; and other compounds processing epitopes. The analyte of interest preferably comprises glucose.

Figure 1:
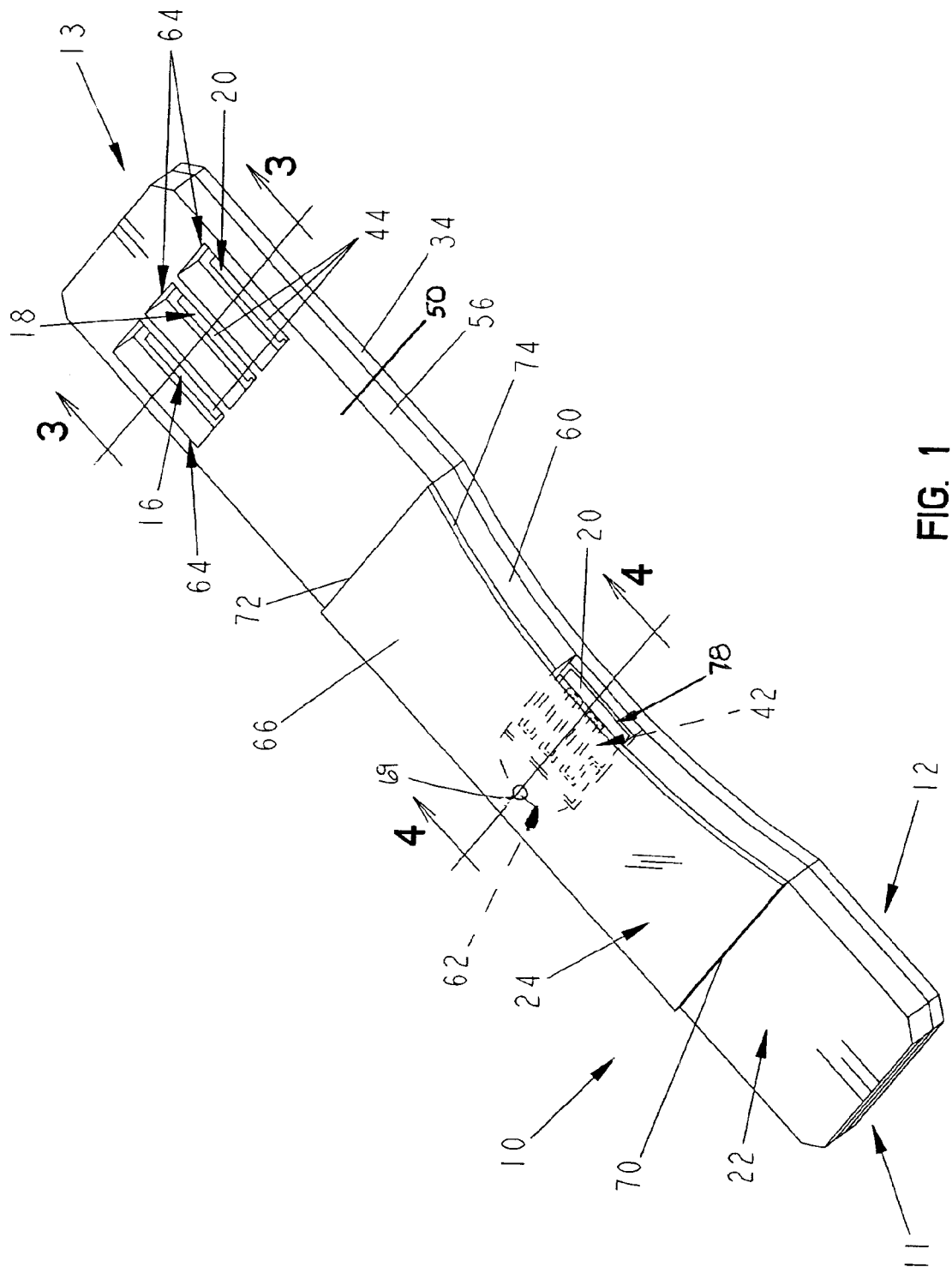
FIG. 1 is a perspective view of a biosensor in accordance with the present invention.
Figure 2A:
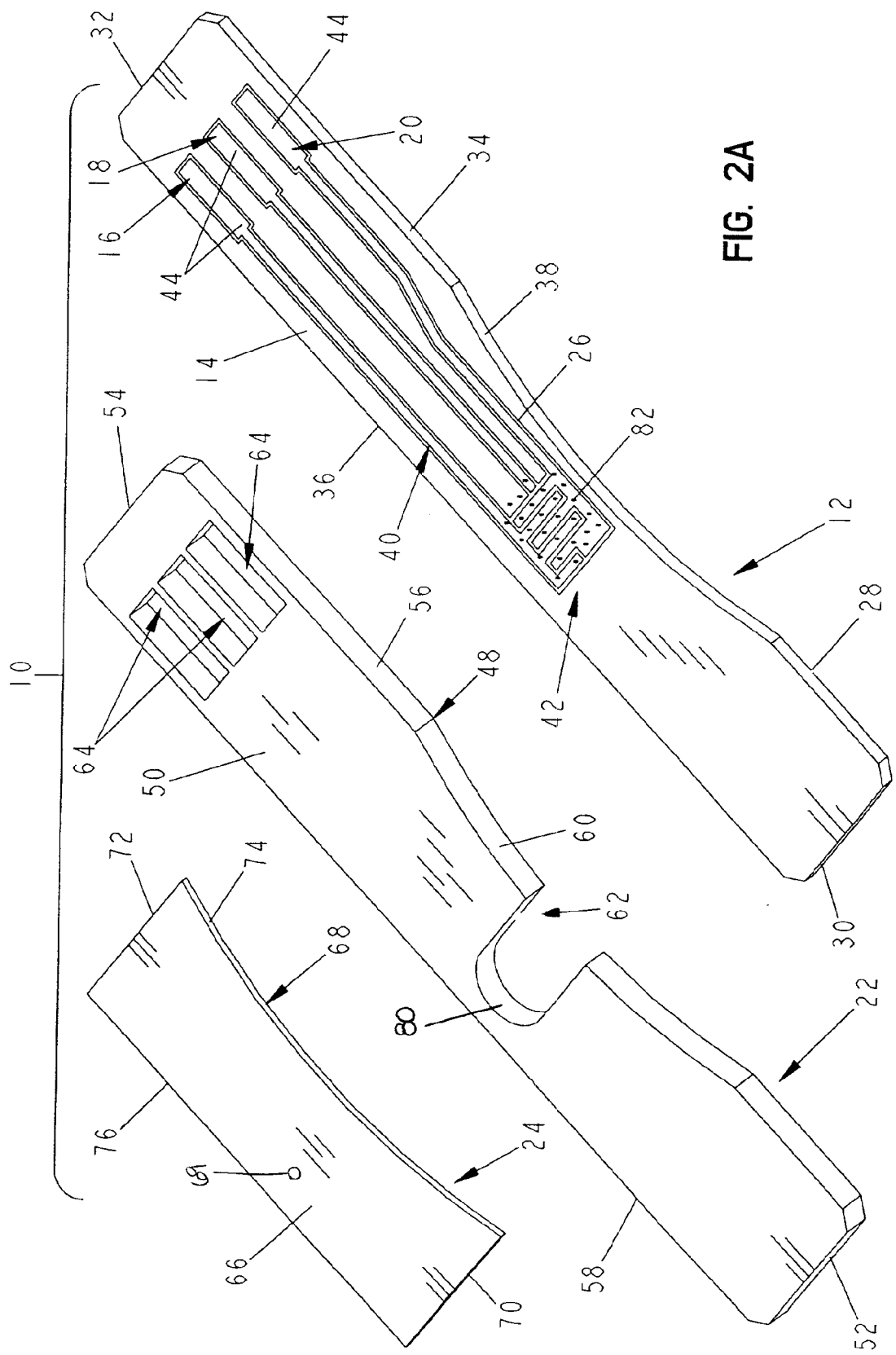
FIG. 2A is an exploded view of the biosensor of FIG. 1.

Biosensor 10 is shown in FIG. 1 and includes opposite ends 11, 13, either of which is available to be grasped by a user without contact with electrodes of the biosensor 10. As shown in FIG. 2A, the biosensor 10 includes an electrode support substrate 12 and an electrical conductor 14 positioned on the substrate 12. The conductor 14 is disrupted to define electrodes 16, 18, 20. Biosensor 10 also includes a sensor support substrate 22 positioned on the substrate 12 and a cover substrate 24 positioned on the sensor support substrate 22. Biosensor 10 is in the form of a disposable test strip. It is appreciated however, that biosensor 10 can assume any number of forms and shapes in accordance with this disclosure.

Biosensor 10 is preferably produced from rolls of material. It is understood that biosensor 10 also can be constructed from individual sheets in accordance with this disclosure. When biosensors 10 are produced from rolls, the selection of materials necessitates the use of materials that are sufficiently flexible for roll processing, but which are still rigid enough to give a useful stiffness to finished biosensor 10.

Referring to FIG. 2A, the electrode support substrate 12 includes a first surface 26 facing the sensor support substrate 22 and a second surface 28. In addition, substrate 12 has opposite first and second ends 30, 32 and opposite edges 34, 36 extending between the first and second ends 30, 32. Edge 34 of substrate 12 is formed to include a generally concave-shaped notch 38. It is appreciated that substrate 12 may be formed without a notch, or that the notch may take on any number of shapes and sizes in accordance with the present disclosure.

Electrode support substrate 12 is generally rectangular in shape, it is appreciated however, that support 12 may be formed in a variety of shapes and sizes in accordance with this disclosure. It is also appreciated that the substrate 12 need not necessarily extend the length of the substrate 22 as shown in FIGS. 1 and 2A. In fact, the substrate 12 can have a shorter length so long as it is of sufficient length to position the electrodes with a channel and windows as will be described hereafter. Substrate 12 may be constructed from a wide variety of insulative materials. Non-limiting examples of insulative materials that provide desirable electrical and structural properties include glass, ceramics, vinyl polymers, polyimides, polyesters, and styrenics. Preferably, substrate 12 is a flexible polymer, such as a polyester or polyimide. A non-limiting example of a suitable material is 5 mil (125 um) thick KALADEX®, a polyethylene naphthalate film commercially available from E. I. DuPont de Nemours, Wilmington, Del., which is coated with gold by ROWO Coating, Henbolzhelm, Germany. It is appreciated that the thickness of the support 12 can be greater or less than 5 mil (125 um) and may be suitable for a number of assembly processes (e.g., lamination, etc.).

Electrodes 16, 18, 20 are created or isolated from conductor 14 on first surface 26 of electrode support substrate 12. See FIGS. 2A and 3. It is appreciated that electrodes 16, 18, 20 can be formed from multiple layers of same or different electrically conductive materials. Non-limiting examples of a suitable electrical conductor 14 include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these elements. Preferably, electrical conductor 14 is selected from the following materials: gold, platinum, palladium, iridium, or alloys of these metals, since such noble metals and their alloys are unreactive in biological systems. Most preferably, the electrical conductor 14 is gold.

Electrodes 16, 18, 20 are isolated from the rest of the electrical conductor 14 by laser ablation. Techniques for forming electrodes on a surface using laser ablation are known. See, for example, U.S. patent application Ser. No. 09/411,940, titled "Laser Defined Features for Patterned Laminates and Electrodes", the disclosure of which is expressly incorporated herein by reference. Preferably, electrodes 16, 18, 20 are created by removing the electrical conductor 14 from an area extending around the electrodes to form a gap 40 of exposed support substrate 12. Therefore, electrodes 16, 18, 20 are isolated from the rest of the electrically-conductive material on substrate 12. Illustratively, the gap 40 has a width of about 25 $\mu$m to about 500 $\mu$m, preferably the gap has a width of about 100 $\mu$m to about 200 $\mu$m. Alternatively, it is appreciated that electrodes 16, 18, 20 may be created by laser ablation alone on substrate 12. It is appreciated that while laser ablation is the preferred method for forming electrodes 16, 18, 20 given its precision and sensitivity, other techniques such as lamination, screen-printing, photolithography, or contact printing may be used in accordance with this disclosure.

As shown in FIG. 2A, electrodes 16, 18, 20 cooperate with one another to define an electrode array 42. In addition, electrodes 16, 18, 20 each include a meter-contact portion 44, a measurement portion positioned in the array 42, and a lead 46 extending between the contact 44 and the measurement portion. Contacts 44 are spaced apart from end 32. It is appreciated that the contacts 44 can be formed to have many lengths and can extend to end 32 or to edges 34, 36, or to any number of locations on substrate 12. Likewise, the leads 38 that extend from the array 34 can be formed to have many lengths and extend to a variety of locations on the electrode support substrate 12. It is appreciated that the configuration of the electrode array, the number of electrodes, as well as the spacing between the electrodes may vary in accordance with this disclosure and that greater than one array may be formed as will be appreciated by one of skill in the art.

As described below, electrodes 16, 18, 20 are used with a reagent to determine the concentration of at least one analyte in a fluid sample. It is appreciated, however, that at least one of the electrodes may be used for purposes other than a reagent-based measurement. A non-limiting example of which includes using one set of leads (either within the reagent or on the bottom side of the sensor) to connect to a thermocouple (not shown) for temperature measurement. Alternatively, depending upon the location of the reagents on the sensor support substrate 22, electrodes are enabled to be used as an antenna for telemetry, or to signify an expiration date, code number, analyte, etc.). It is also contemplated by the present disclosure to use the electrodes to examine a ratio of currents at one or more time points to determine if the biosensor 10 has been exposed to inappropriate temperature, humidity, interferents, etc.).

Figure 2B:
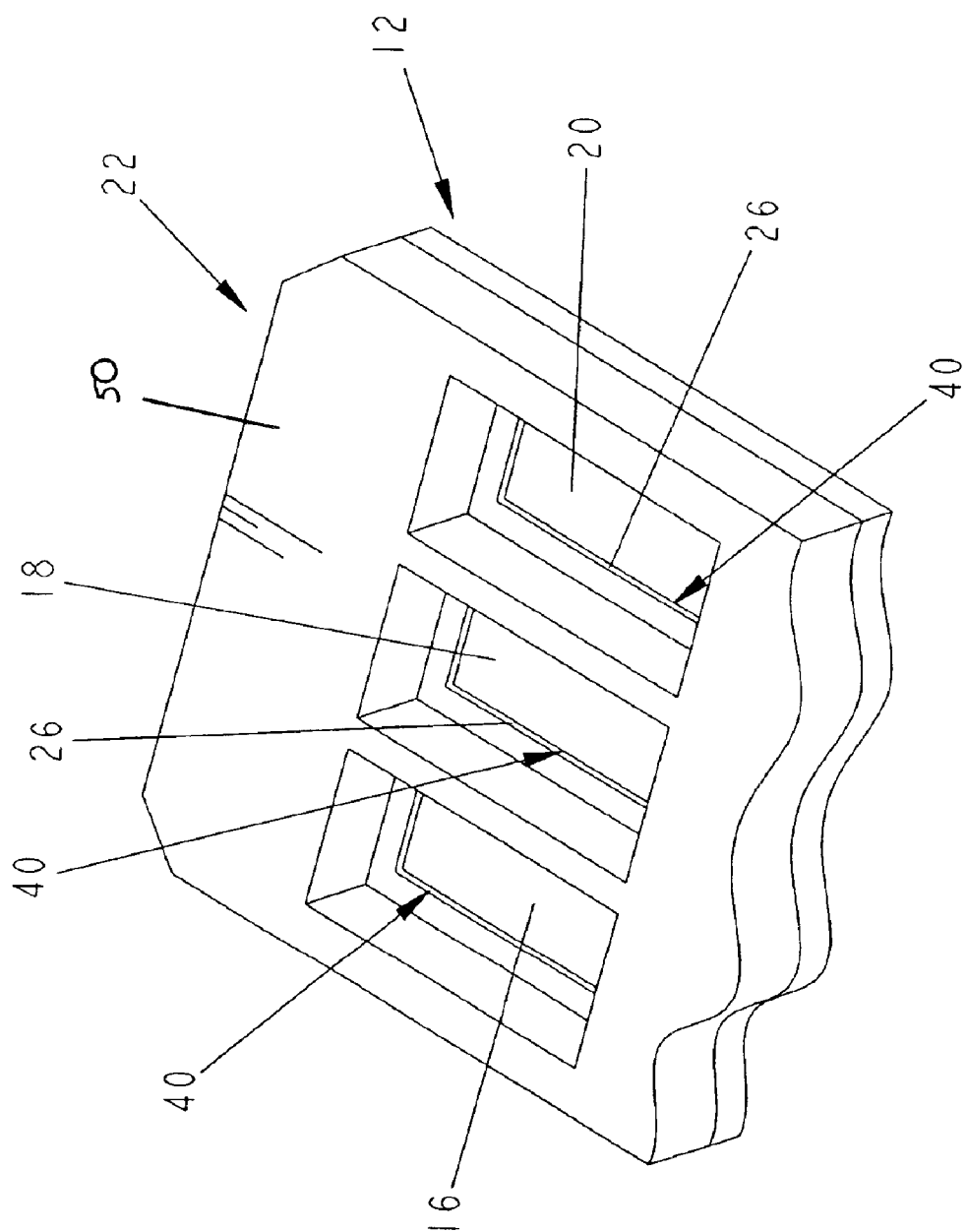
FIG. 2B is an enlarged assembled view of a portion of the biosensor of FIG. 2 illustrating three discrete windows.
Figure 3:
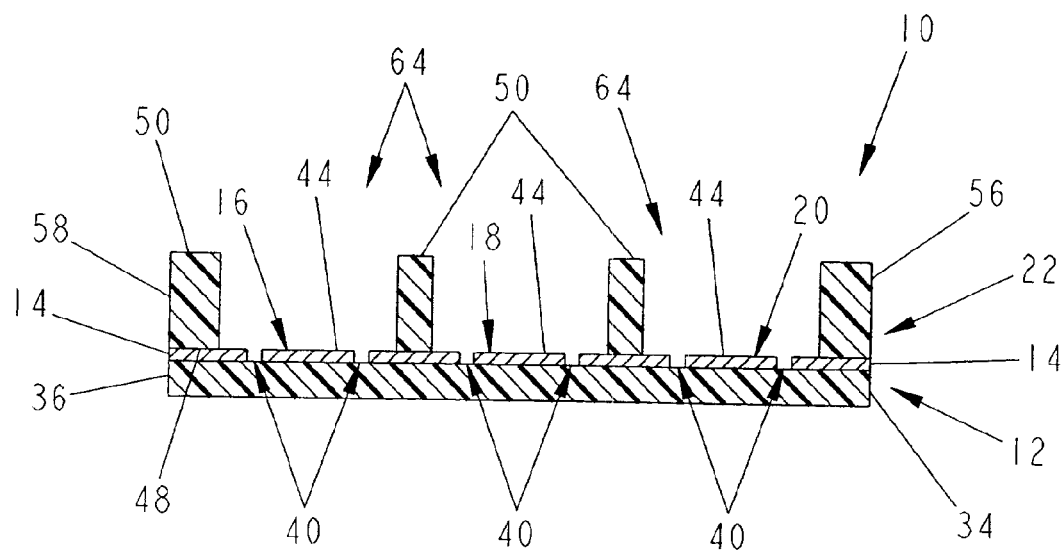
FIG. 3 is a view taken along lines 3—3 of FIG. 1.
Figure 4:
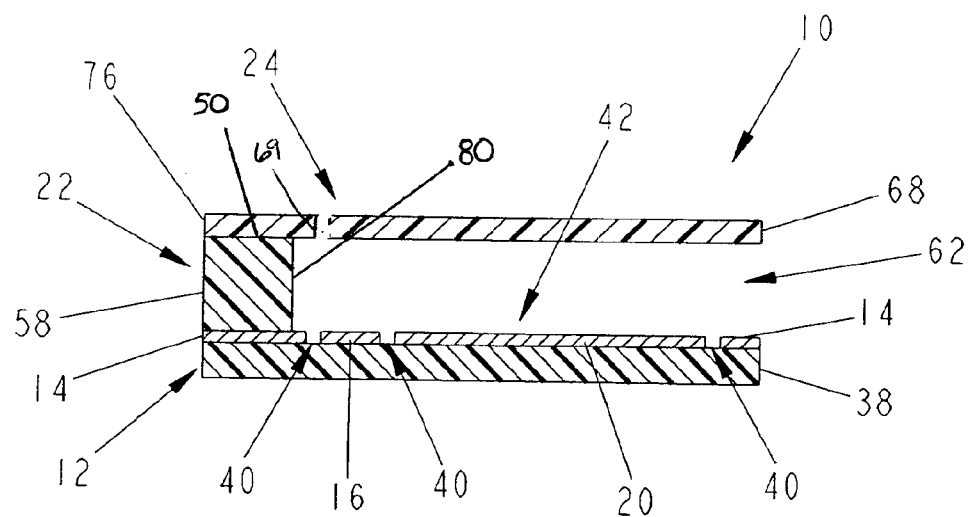
FIG. 4 is a view taken alone lines 4—4 of FIG. 1.

As shown in FIG. 2B, the sensor support substrate 22 of biosensor 10 extends to the end 32 of substrate 12 to permit a user to grasp the end 11 of biosensor 10 without contacting the electrodes 16, 18, 20. It is appreciated, however, that substrate 32 may extend past end 32 in accordance with this disclosure. The sensor support substrate 22 is positioned to lie between the electrode support substrate 12 and the cover substrate 24. Referring now to FIG. 4, the sensor support substrate 22 cooperates with the support substrate 12 and the cover 24 to expose the electrode array 42 to a liquid sample (not shown) being applied to the biosensor 10. Sensor support substrate 22 can be formed from any number of commercially available insulative materials. Non-limiting examples of insulative materials that provide desirable electrical and structural properties include vinyl polymers, polyimides, polyesters, and styrenics. Preferably, the sensor support substrate 22 is 10 mil (250 um) thick opaque white MELINEX® 329 plastic, a polyester commercially available from E. I. DuPont de Nemours, Wilmington, Del., which is coated with a thermoplastic resin (Griltex D 1698 E), commercially available from EMS-Chemie (North America) Inc., Sumter, S.C. It is further appreciated that sensor support substrate 22 may be formed of a double-sided adhesive tape covered by an insulative material in accordance with the disclosure, so long as it is of a sufficient thickness to create a detent about at least one window 64, as will be described below.

Referring now to FIG. 2A, the sensor support substrate 22 includes a first surface 48 and a second surface 50 facing the electrode support substrate 12. When the sensor support substrate 22 is coupled to the substrate 12 a first end 52 of the sensor support substrate 22 is aligned with end 30, a second end 54 is aligned with end 32, an edge 56 is aligned with edge 34, and an opposite edge 58 is aligned with edge 36.

Further, the edge 56 is formed to include a notch 60 that is shaped so as to be aligned with notch 38 of the substrate 12. It is appreciated that substrate 12 may be formed without a notch, or that the notch may take on any number of shapes and sizes in accordance with the present disclosure. An opening 62 extends from the notch 60 toward the edge 58. When the sensor support substrate 22 is coupled to the substrate 12, as shown in FIGS. 1 and 4, the substrates 12, 22 cooperate to define a channel aligned with the electrodes. Thus, upon assembly, the measurement portion of the electrodes that cooperate to form the electrode array 42 are positioned to lie in general alignment with the opening 62 and are thus positioned in the channel 78 to expose at least a portion of the electrodes 16, 18, 20 of the electrode array 42. An interior border 80 defines the opening 62. The width of the interior border 80 can vary in accordance with this disclosure.

The sensor support substrate 22 extends to the end 32 of substrate 12 and is formed to expose the electrode contacts 44 for engagement with a meter 124. A non-limiting example of such a meter is shown diagrammatically in FIG. 10. Referring now to FIG. 1, sensor support substrate 22 includes windows 64 that extend between first and second surfaces 48, 50. Each window 64 creates a detent in sensor support substrate 22 and is spaced apart from end 54. This detent provides mechanical feedback for strip mating with meter contacts and increases the rigidity of the substrate 22. Further, the positioning of the windows 64 enables a user to grasp the end 11 of the biosensor 10 without touching the electrode contacts 44. Thus, the inadvertent deposit of skin oils, dirt, skin cells, etc. onto the electrical contacts 44 through simple handling of the biosensor 10 is prevented.

In addition, at least one window 64 may be used to perform alignment of the substrates 12 and 22. It is also appreciated that at least one window 64 may be used to perform alignment for other manufacturing processes such as dispensing, labeling, cutting, punching, etc. Moreover, it is appreciated that windows 64 can take on a variety of shapes and sizes in accordance with the present disclosure. Illustratively, windows 64 are formed to be slightly larger than the respective contacts 44. A non-limiting example of dimensions of suitable windows 64 when contacts have a width of about 1 mm and a length of about 2 mm, is a width of about 1.5 mm and a length of about 2.5 mm. In addition, while three windows 64 are shown, it is appreciated that biosensor 10 can be formed with greater than three windows or as few as one window in accordance with the present disclosure. Non-limiting examples of which include windows illustrated in FIGS. 8–10, and 13–15.

Sensor support substrate 22 is coupled to the electrode support substrate 12 as shown in FIG. 1. The thermoplastic resin on surface 48 permits the substrate 22 to be heat-sealed to the conductor 14 coating substrate 12. It is appreciated that substrates 12 and 22 may be coupled together using a wide variety of commercially available adhesives or with welding (heat or ultrasonic on portions of substrate 12 where the conductor 14 has been removed) in accordance with this disclosure. It is also appreciated that first surface 50 of substrate 22 may be printed with, for example, product labeling or instructions for use in accordance with this disclosure.

The cover substrate 24 is coupled to the spacer support 22 across the opening 62. See FIG. 1. The cover substrate 24 of biosensor 10 includes a first surface 66 facing substrate 12, an opposite second surface 68 and a vent 69 extending between surfaces 66, 68. In addition, cover substrate 24 has opposite first and second ends 70, 72 and edges 74, 76 extending between ends 70, 72. Edge 74 is preferably generally concave shape for alignment with notches 38, 60 of substrates 12, 22 respectively. It is appreciated, however, that the edge 74 may take on any number of shapes and sizes in order to be in general alignment with the shape of notches 38, 60. The cover substrate 24 is formed of a flexible polymer and preferably from a polymer such as an adhesive coated polyethylene terephthalate (PET)—polyester. A non-limiting example of a suitable PET is 2 mil (50 um) thick clear PET film one side of which is coated with a hydrophilic pressure-sensitive adhesive (Product #ARcare 8877) commercially available from Adhesives Research, Inc. Glen Rock, Pa.

The cover substrate 24 is formed to cooperate with the sensor support substrate 22 and the support substrate 12 to define a channel 78 extending from edges 34, 56, 74 and across the electrode array 42. The channel 78 is preferably a capillary channel that is formed to transport a fluid sample from the user to the electrode array 42. As shown in FIG. 4, the channel 78 extends from edges 34, 56, 74 and is defined by the interior border 80 of the opening 62. It is appreciated that the channel 78 can extend from any number of locations of biosensor 10 to the array 42. It is also appreciated that channel 78 may also be formed from cooperation between only the sensor support substrate 22 and the support substrate 12.

An electrochemical reagent 82 is positioned on the array 42. The reagent 82 provides electrochemical probes for specific analytes. The choice of the specific reagent 82 depends on the specific analyte or analytes to be measured, and are well known to those of ordinary skill in the art. An example of a reagent that may be used in biosensor 10 of the present invention is a reagent for measuring glucose from a whole blood sample. A non-limiting example of a reagent for measurement of glucose in a human blood sample contains 62.2 mg polyethylene oxide (mean molecular weight of 100–900 kilo Daltons), 3.3 mg NATROSOL 244M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase. This reagent is further described in U.S. Pat. No. 5,997,817, the disclosure of which is expressly incorporated herein by reference.

Non-limiting examples of enzymes and mediators that may be used in measuring particular analytes in biosensor 10 are listed below in Table 1.

TABLE 1

| Analyte | Enzymes | Mediator (Oxidized Form) | Additional Mediator |
| --- | --- | --- | --- |
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is contemplated that current, charge, impedance, conductance, potential, or other electrochemically indicated property of the sample might be accurately correlated to the concentration of the analyte in the sample with biosensor 10 in accordance with this disclosure.

A plurality of biosensors 10 are typically packaged in a vial, usually with a stopper formed to seal the vial. It is appreciated, however, that biosensors 10 may be packaged individually, or biosensors can be folded upon one another, rolled in a coil, stacked in a cassette magazine, or packed in blister packaging.

Biosensor 10 is used in conjunction with the following:
1. a power source in electrical connection with contacts 44 and capable of supplying an electrical potential difference between electrodes 16, 18, 20 sufficient to cause diffusion limited electro-oxidation of the reduced form of the mediator at the surface of the working electrode; and
2. a meter in electrical connection with contacts 44 and capable of measuring the diffusion limited current produced by oxidation of the reduced form of the mediator with the above-stated electrical potential difference is applied.

The meter will normally be adapted to apply an algorithm to the current measurement, whereby an analyte concentration is provided and visually displayed. Improvements in such power source, meter, and biosensor system are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of each of which are expressly hereby incorporated by reference.

Many fluid samples may be analyzed. For example, human body fluids such as whole blood, plasma, sera, lymph, bile, urine, semen, cerebrospinal fluid, spinal fluid, lacrimal fluid and stool specimens as well as other biological fluids readily apparent to one skilled in the art may be measured. Fluid preparations of tissues can also be assayed, along with foods, fermentation products and environmental substances, which potentially contain environmental contaminants. Preferably, whole blood is assayed with this invention.

Figure 5:
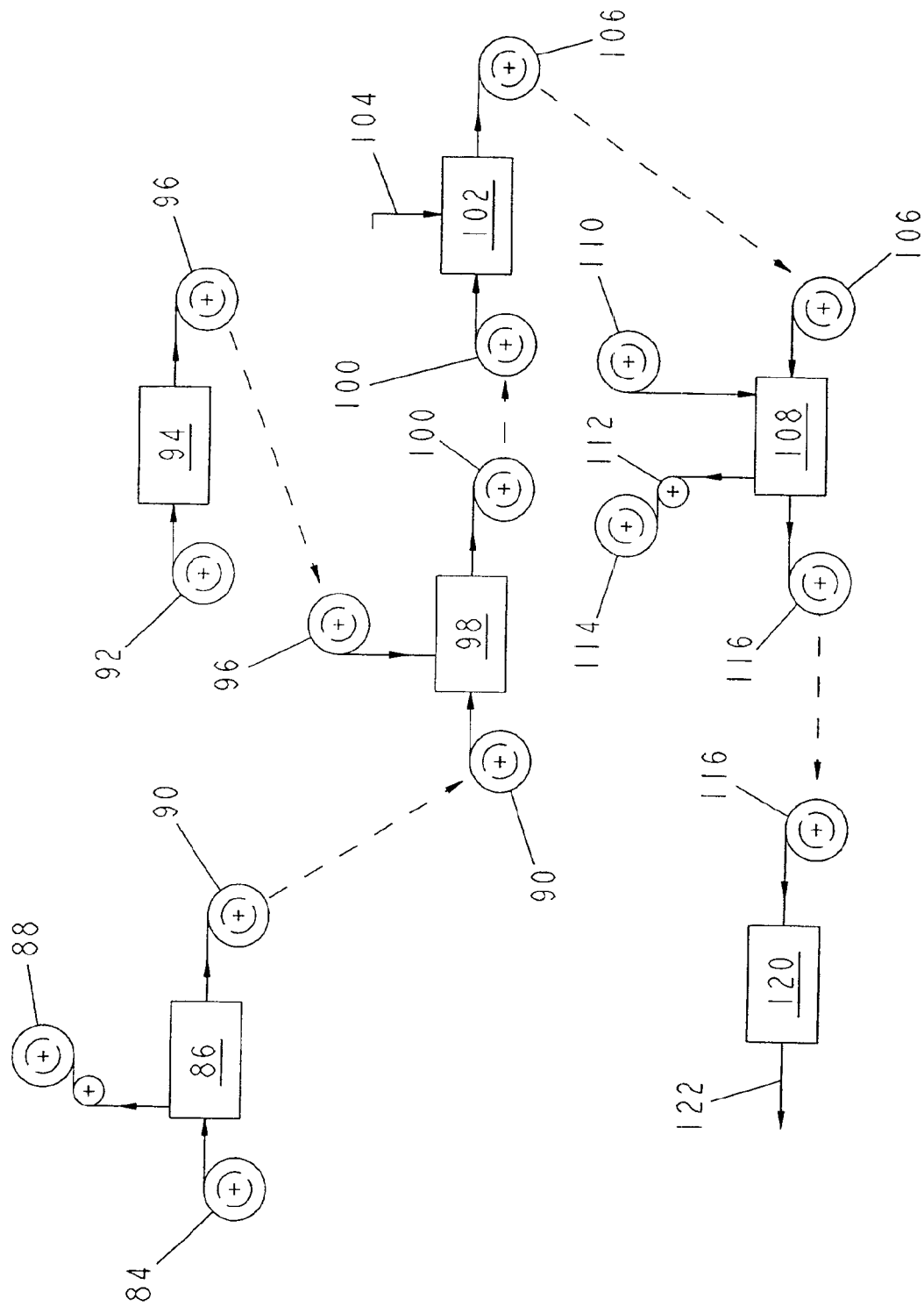
FIG. 5 is a diagrammatic view of the method of manufacturing the biosensor of the present invention.

As shown in FIG. 5, biosensor 10 is manufactured using six distinct processes. In process one, a roll of sensor support substrate material 84 is fed into a window punch and web slit station 86. In the station 86, the windows 64 and the opening 62 are created through the sensor support substrates in the web and the web is slit to its final dimension in the station. The trim, from the edges of the web of material is removed from the material and wound into a roll 88. Upon leaving the station 86, the punched sensor support substrates connected to one another via a web are wound into a roll 90.

In process two, a roll of metallized electrode support material 92 is fed into an ablation/washing and drying station 94. A laser system capable of ablating support 12 is known to those of ordinary skill in the art. Non-limiting examples of which include excimer lasers, with the pattern of ablation controlled by mirrors, lenses, and masks. A non-limiting example of such a custom fit system is the LPX-300 or LPX-200 both commercially available from LPKF Laser Electronic GmbH, of Garbsen, Germany.

In the ablation station 94, the metallic layer of the metallized film is ablated in a pre-determined pattern, to form a ribbon of support material with isolated electrode patterns 96. To ablate electrodes 16, 18, 20 isolated by gaps 40 in 50 nm thick gold conductor 14, 90 mJ/cm² energy is applied. It is appreciated, however, that the amount of energy required may vary from material to material, metal to metal, or thickness to thickness. If however, any seed layer or other metallic layer such as Crominium or Titanium or any other metal is used for any purpose, and then gold is put down, the total thickness of all composite metals is still preferred to be about 50 nm. It is appreciated that the total thickness may vary between about 30 and about 80 nm in accordance with this disclosure. In the ablation station 94, the ribbon is also passed through an optional inspection system where both optical and electrical inspection can be made. The system is used for quality control in order to check for defects.

Next, in process three, the roll of punched sensor support substrates 90 is fed into a cutting and lamination station 98. At the same time, the ribbon of support material with isolated electrode patterns 96 is fed into the station 98. The thermoplastic resin coated first surface of the sensor support substrates 90 is applied to the electrode support substrate material so that the windows 64 are in general alignment with the respective contacts 44 and the openings 62 are in general alignment with the arrays 42. It is appreciated that the windows 64 may in fact be used as a built-in fiducial for alignment the sensor support substrates 90 with the ribbon of support material. Once aligned, the web of sensor support substrates 90 is heat-sealed to the ribbon of support material 96 to form subassembly 100.

In process four, the subassembly 100 is fed into a reagent dispensing station 102. A reagent that has been compounded is fed, as shown by arrow 104, into the dispensing station 102 where it is applied in a liquid form in multiple shots to the array 42. It is appreciated, however, that the reagent can be applied in a single shot by a custom fit precision dispensing station available from Fluilogic Systems Oy, Espoo, Findland. Reagent application techniques are well known to one of ordinary skill in the art as described in U.S. Pat. No. 5,762,770, the disclosure of which is expressly incorporated herein by reference. It is appreciated that reagents may be applied to the array 42 in a liquid or other form and dried or semi-dried onto the array 42 in accordance with this disclosure. A reagent-coated subassembly 106 then exits the station 102.

In process five, the reagent-coated subassembly 106 is fed into a second cutting and lamination station 108. At the same time, a ribbon of cover material 110 is fed into station 108. A liner on one side of the ribbon 10 is removed in the station 108 and rewound over guide roll 112 into a roll 114 for discard. The ribbon of cover material 110 and the subassembly 106 are aligned so that the cover material 110 lies across the electrode arrays 42 to form an assembled material 116.

In process six, the assembled material 116 is fed into a sensor punch/pack station 120 where the material 116 is cut to form individual biosensors 10. The biosensors 110 are sorted and packed into vials. Each vial is then closed with a stopper to give packaged biosensor strips as shown by arrow 122.

In use, for example, a user of biosensor 10 places a finger having a blood collection incision against respective notches 38, 60 and edge 74 adjacent opening 62. Capillary forces pull a liquid sample flowing from the incision into the opening 62 and through the capillary channel 78 across the reagent 82 and the array 42. The liquid sample dissolves the reagent 82 and engages the array 42 where the electrochemical reaction takes place.

The user then inserts the biosensor 10 into the meter 124 (see, for example FIG. 10) where an electrical connection is made between the electrode contacts 44 exposed by windows 64 and three corresponding meter contacts 126 of the meter 124. Referring now to FIG. 11, a non-limiting example of a suitable meter contact 126 is illustrated. Meter contact 126 includes an electrode engagement portion 128 that is formed of an electrically conductive material and a pivot portion 130. Each meter contact 126 is spring-loaded so that it pivots over the edge 54 of the spacer support substrate 22 when the biosensor 10 is moved into the meter 124, as shown for example by arrow 132, and rides across the surface 50 of said substrate. When, however, the electrode engagement portion 128 encounters a window 64, the meter contact 126 pivots on the pivot portion 130 so that the portion 128 engages a corresponding electrode exposed by the window 64 and creates an electrically conductive connection between the exposed electrode and the contact. It is appreciated that the illustrated meter 124 includes greater than three meter contacts 126, two of which will rest upon the second surface 50 of the spacer substrate 22 when the biosensor 10 is inserted into the meter 124. It is appreciated that biosensor 10 may be used with a variety of meters, which may include greater or less than five meter contacts in accordance with this disclosure.

Moreover, it is appreciated that the biosensor 10 also may be inserted into the meter 124 at a variety of time periods including prior to the sample flowing into the opening 62. Once the electrochemical reaction is complete, a power source (e.g., a battery) applies a potential difference between the electrodes 16, 18, 20 respectively. When the potential difference is applied, the amount of oxidized form of the mediator at the reference electrode and the potential difference must be sufficient to cause diffusion limited electrooxidation of the reduced form of the mediator at the surface of the working electrode. The current measuring meter 124 measures the diffusion-limited current generated by the oxidation of the reduced form of the mediator at the surface of the working electrode as described above.

The measured current may be accurately correlated to the concentration of the analyte in sample when the following requirements are satisfied:

1. The rate of oxidation of the reduced form of the mediator is governed by the rate of diffusion of the reduced form of the mediator to the surface of the working electrode.

2. The current produced is limited by the oxidation of reduced form of the mediator at the surface of the working electrode.

It is appreciated that the meter 124 can be designed to be utilized with a number of different biosensors with a variety of different electrodes or contacts. Non-limiting examples of alternative biosensors may require temperature or hematocrit compensation, others might utilize a one, two, four, five or more electrode configuration, others might require coding or expiration information exchange with the meter, etc. Furthermore, the meter 124 may be formed to measure multiple analytes simultaneously on a single strip (e.g., glucose and fructosamine, glucose and ketones, HDL and total cholesterol, etc.). For example, the presence and location of the contacts 44 exposed through the windows 64 could readily identify such a biosensor to the meter as a glucose/ketone assay). Thus, by using different combinations of window placement on biosensor 10, new analytes may easily be added to the meter's applications.

Figure 6:
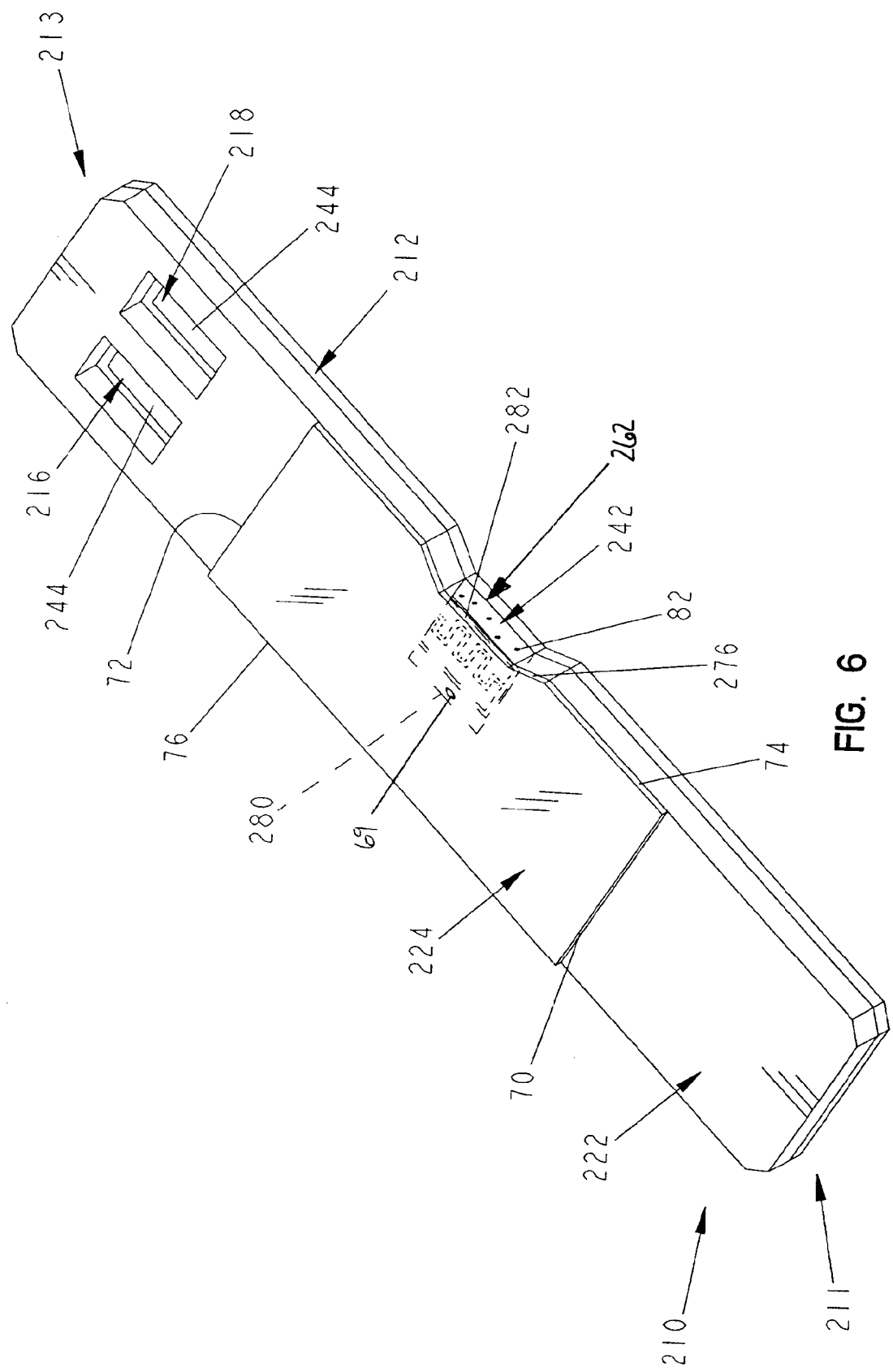
FIG. 6 is a perspective view of a biosensor in accordance with another aspect of the present invention.
Figure 7:
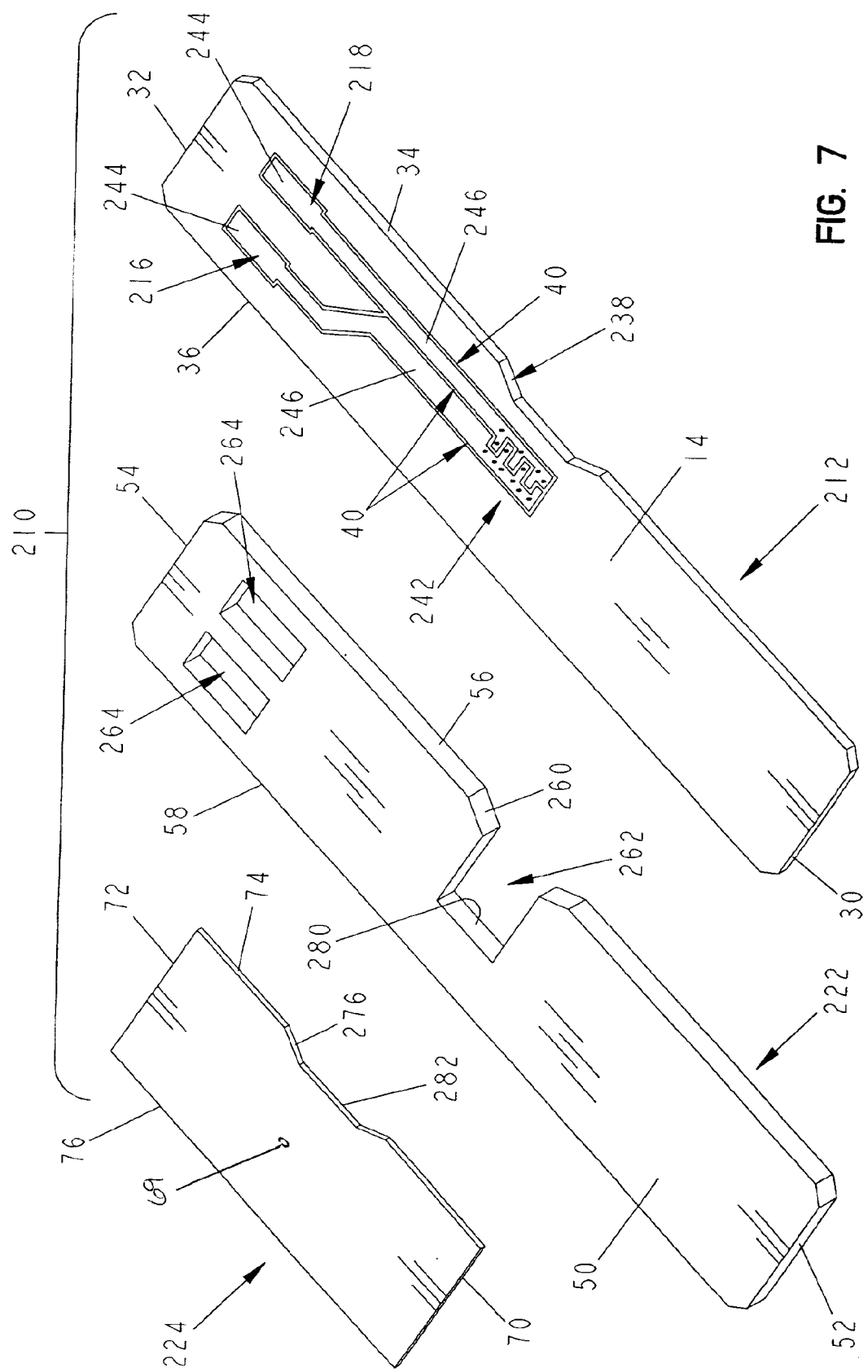
FIG. 7 is an exploded view of the biosensor of FIG. 6.

In another aspect of the invention, a biosensor 210 is provided in accordance with the present invention. Biosensor 210 is shown in FIGS. 6–7 and includes opposite ends 211, 213, either of which is available to be grasped by a user without contact with electrodes of the biosensor 210. Biosensor 210 includes an electrode support substrate 212 that supports the electrical conductor 14 described above with reference to biosensor 10. The conductor 14 is disrupted to define electrodes 216, 218. Biosensor 210 also includes a sensor support substrate 222 positioned on the substrate 212 and a cover substrate 224 positioned on the sensor support substrate 222. Biosensor 210 is formed in a variety of shapes and sizes and from materials similar to biosensor 10 as described above.

Referring to FIG. 7, the edge 34 of the electrode support substrate 212 is formed to include a notch 238. It is appreciated that substrate 212 may be formed without a notch, or that the notch may take on any number of shapes and sizes in accordance with the present disclosure. Electrodes 216, 218 are created or isolated from conductor 14 similar to electrodes 16, 18, 20 as described above. Electrodes 216, 218 cooperate with one another to define an electrode array 242. In addition, electrodes 216, 218 each include a contact 244 and a lead 246 extending between the contact 244 and the array 242. Contacts 244 are spaced apart from end 32. It is appreciated that the contacts 244 can be formed to have many lengths and can extend to end 32 or to edges 34, 36, or to any number of locations on substrate 212. Likewise, the leads 246 that extend from the array 242 can be formed to have many lengths and extend to a variety of locations on the electrode support substrate 12. It is appreciated that the configuration of the electrode array, the number of electrodes, as well as the spacing between the electrodes may vary in accordance with this disclosure and that a greater than one array may be formed as will be appreciated by one of skill in the art.

Sensor support substrate 222 of biosensor 210 is positioned to lie between support substrate 212 and cover substrate 224. Sensor support substrate 222 extends to the end 32 to permit a user to grasp the end 213 of the biosensor 210 without touching the electrodes 216, 218. Moreover, the sensor support substrate 222 cooperates with the support substrate 212 and the cover 224 to expose the electrode array 242 to a liquid sample being applied to the biosensor 210. Sensor support substrate 222 may have a variety of lengths and is formed from materials similar to substrate 22, as described above.

As shown in FIG. 7, the edge 56 of the sensor support substrate 22 is formed to include a notch 260. It is appreciated that substrate 212 may be formed without a notch, or that the notch may take on any number of shapes and sizes in accordance with the present disclosure. An opening 262 extends from the notch 260 toward the edge 58. When the sensor support substrate 222 is coupled to substrate 212, the electrode array 242 is positioned to lie in general alignment with the opening 262, exposing at least a portion of the electrode array 242. An interior border 280 defines the opening 262. The width of the interior border 280 can vary in accordance with this disclosure.

The sensor support substrate 222 extends to the end 32 of substrate 212 and is formed to expose the electrode contacts 244 for engagement with a meter 282, as shown for example in FIG. 9. Referring now to FIGS. 7 and 9, the sensor support substrate 222 includes discrete windows 264 that extend between first and second surfaces 48, 50. Each window 264 is spaced apart from end 54 in order to enable a user to grasp the end 54 of the sensor support substrate 222 without touching the electrode contacts 244. Thus, the inadvertent deposit of skin oils, dirt, skin cells, etc. onto the electrical contacts 244 through simple handling of the biosensor 210 is prevented. In addition, at least one window 264 may be used to perform alignment of the substrates 212 and 222. It is also appreciated that at least one window 264 may be used to perform alignment for other manufacturing processes such as dispensing, labeling, cutting, punching, etc. Moreover, it is appreciated that windows 264 can take on a variety of shapes and sizes as described above with reference to windows 64 in accordance with the present disclosure.

As show in FIG. 6, the cover substrate 224 is coupled to the spacer support 222 and extends across the opening 262. The edge 74 of the cover substrate 224 formed to include a notch 276. It is appreciated that substrate 224 may be formed without a notch, or that the notch may take on any number of shapes and sizes in accordance with the present disclosure. When the cover substrate 224 is coupled to the sensor support substrate 222, an interior border 282 is aligned with the entrance to the opening 262. The width of the interior border 282 can vary in accordance with this disclosure.

Biosensor 210 is manufactured in a similar manner to biosensor 10, except for the following differences: First, in the window punch and web slit station 86, two windows 264 and an opening 262 that has a border 280 with corners are formed in the web of the sensor support substrate 90. Second, in the ablation/washing and drying station 94, two electrodes 216, 218 are formed on the substrate 212. Cover material 110 is then fed into the second cutting and lamination station 108 along with the reagent-coated subassembly 106 as discussed above with reference to biosensor 10. In addition, the ribbon of the cover material 110 and the subassembly 106 are aligned to form an assembled material 116. The assembled material 116 is then fed into the sensor punch/pack station 120 where the material 116 is cut to form individual biosensors 210 and packed as described above with reference to biosensors 10.

In use, for example, a user of biosensor 210 places a finger having a blood collection incision against array 242 exposed by opening 262. The liquid sample flowing from the incision dissolves the reagent 82 and engages the array 42 where the electrochemical reaction takes place. Cooperation between the biosensor 210 and the meter 282 are similar to that described above with reference to biosensor 10. Meter 282, however, includes two meter contacts 126. Each meter contact 126 is formed to pivot over edge 54 of the sensor support substrate 222 when the biosensor 210 is inserted into the meter 282. These meter contacts 126 ride across the surface 50 and pivot into aligned windows 264 so that the portion 128 engages a corresponding electrode exposed by the window 264 and creates an electrically conductive connection between the exposed electrode and the contact.

In accordance with another aspect of the present invention, a biosensor 310 is provided and is illustrated in FIG. 8. The biosensor 310 is constructed and manufactured identically to biosensor 210 except its spacer support substrate 222 is formed to include one window 364. This window 364 exposes both electrodes 216, 218 to a meter, such as the meter 282 illustrated in FIG. 9. Biosensor 310 is also used in a manner similar to biosensor 210, except that upon insertion of the biosensor 310 into the meter 282, the meter contacts 126 each pivot into the single window 364 for engagement with an aligned electrode to create an electrically conductive connection between the exposed electrode and the contact.

In accordance with another aspect of the present invention, a biosensor 410 is provided and is illustrated in FIGS. 10–12. As shown in FIGS. 11 and 12, biosensor 410 includes an electrode support substrate 412 that supports the electrical conductor 14 as described above with reference to biosensor 10. Referring now to FIG. 10, the conductor 14 is disrupted to define electrodes 416, 418, 420, 422, 426. Biosensor 410 also includes a sensor support substrate 422 positioned on the substrate 412. Biosensor 410 may also include a cover substrate, as shown for example in FIGS. 2 and 7, positioned on the sensor support substrate 422. Biosensor 410 is formed in a variety of shapes and sizes and from materials similar to biosensor 10 as described above.

Electrodes 416, 418, 420, 422, 426 are created or isolated from conductor 14 similar to electrodes 16, 18, 20 as described above. Each electrode 416, 418, 420, 422, 426 includes a contact 444 spaced apart from end 32 and a lead 446 extending from the contact 444. It is appreciated that the contacts 444 can be formed to have many lengths and can extend to any number of locations on substrate 212. Likewise, the leads 246 that extend from the contacts 444 can be formed to have many lengths and extend to a variety of locations on the electrode support substrate 412. It is appreciated that the configuration of the electrodes may vary as discussed above with reference to biosensors 10, 210, 310.

Sensor support substrate 422 of biosensor 410 extends to the end 32 of the electrode support substrate 412. Substrate 422, may however have a variety of lengths and be formed from materials similar to substrate 22, as described above. In addition, the sensor support substrate 422 is formed to expose the electrode contacts 444 for engagement with the meter 124. As shown in FIG. 10, the sensor support substrate 422 includes five discrete windows 464. Windows 464 extend between first and second surfaces 48, 50. Each window 264 is spaced apart from end 54. Similar to windows 64, 264, at least one window 264 may be used to perform alignment for a variety of manufacturing processes. Moreover, it is appreciated that windows 464 can take on a variety of shapes and sizes as described above with reference to windows 64 in accordance with the present disclosure.

Biosensor 410 is manufactured in a similar manner to biosensor 210, except for the following differences: First, in the window punch and web slit station 86, five windows 464 are formed in the web of the sensor support substrate 90. Second, in the ablation/washing and drying station 94, five electrodes 416, 418, 420, 424, 426 are formed on the substrate 412.

The biosensor 410 is used in a manner similar to biosensors 10, 210, 310. In addition, cooperation between the biosensor 410 and the meter 124 are similar to that described above with reference to biosensor 10. Each meter contact 126 is formed to pivot over edge 54 of the sensor support substrate 422 when the biosensor 410 is inserted into the meter 124. These meter contacts 126 ride across the surface 50 and pivot into aligned windows 464 so that the portion 128 engages a corresponding electrode exposed by the window 464 and creates an electrically conductive connection between the exposed electrode and the contact.

A non-limiting example of an alternative to meter contact 126 is illustrated diagrammatically in FIG. 12. The alternative meter contact 466 may be a mechanical switch or an optical (LED) switch. Contact 466 may be used for an automatic on/off switch, to signify which type of biosensor has been inserted into the meter, as a fail safe for the meter contact, and/or as a positive mating mechanism. It is appreciated that a variety of commercially available mechanical switches and LED switches may be used in accordance with this disclosure.

In use, the meter is turned on and the biosensor is inserted into the meter. It is appreciated that the user may turn on the meter, or it may turn on automatically upon insertion of the biosensor. The LED emits a light that is directed through a lens towards the biosensor. The light is reflected off of the exposed conductor 14, through the lens, and toward the photodiode. The photodiode measures the intensity of the light that is reflected back from the conductor 14 and generates a corresponding voltage waveform. A decoder deciphers this waveform and translates it into a reading of the conductor. It is appreciated that many commercially available optical readers may be used in accordance with the present invention. Preferably, the optical reader will be a custom fit reader.

In addition, in accordance with another aspect of the present invention, a biosensor 510 is provided and is illustrated in FIG. 13. The biosensor 510 is constructed and manufactured identically to biosensor 410 except its spacer support substrate 522 is formed to include four windows 564 instead of five. Thus, one electrode, a non-limiting example of which is electrode 416, remains covered by the spacer support substrate 522. It is appreciated that greater than one electrode may be covered by the substrate 522. Biosensor 510 is used in a manner similar to biosensor 410, except that upon insertion of the biosensor 510 into the meter 124, four meter contacts 126 pivot into corresponding windows 464 for engagement with aligned electrodes 418, 420, 424, 426 to create an electrically conductive connection between the exposed electrodes and the contacts. The meter contact 126 that is aligned with electrode 416 remains resting upon the second surface 50 of the spacer support substrate 522.

Figure 14:
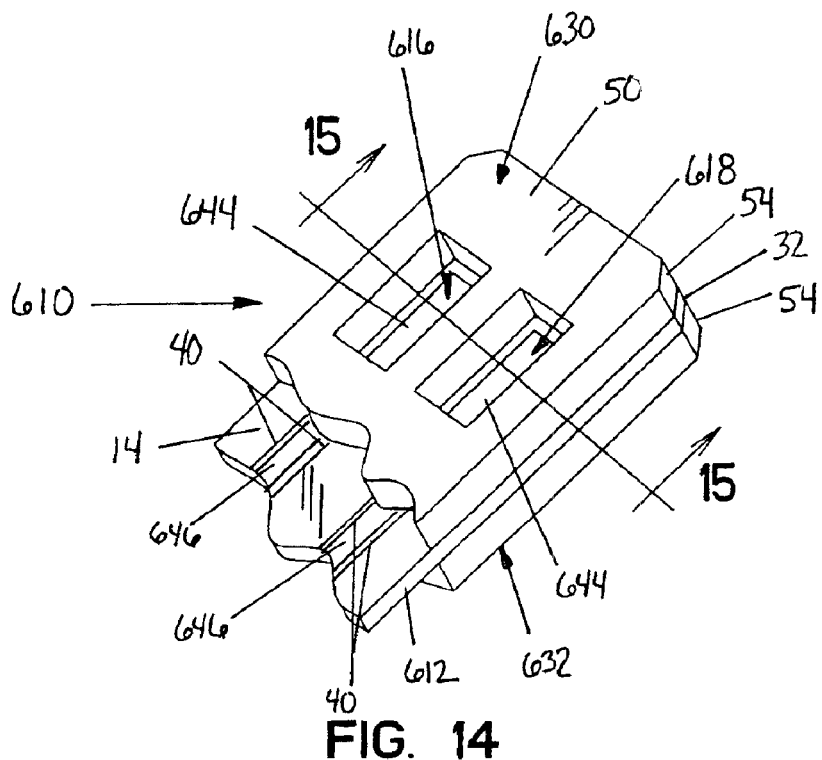
FIG. 14 is an enlarged perspective view of a biosensor in accordance with another aspect of the present invention.
Figure 15:
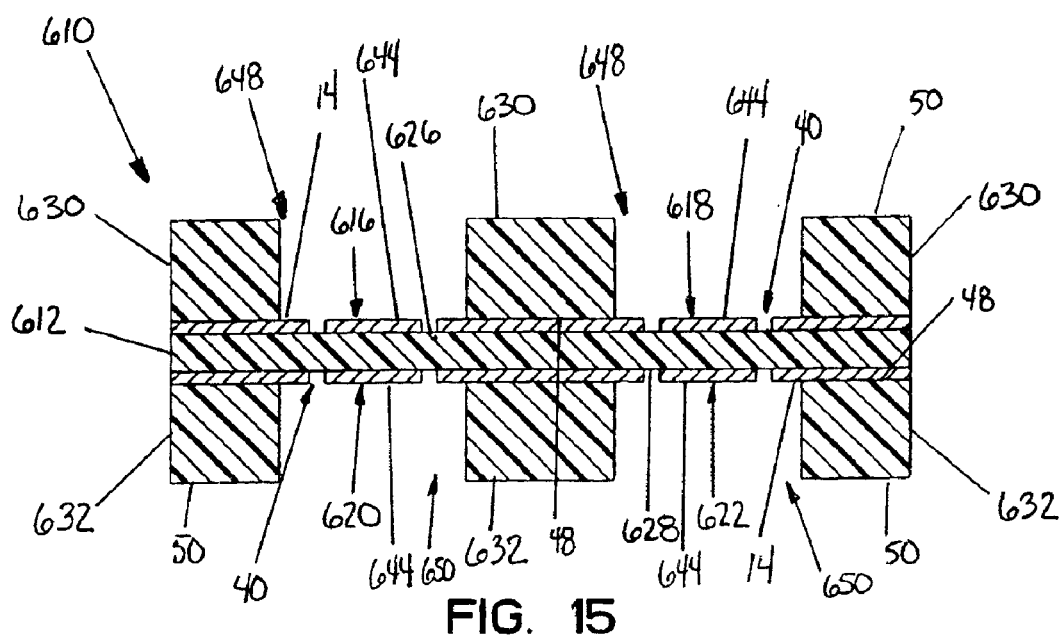
FIG. 15 is a view taken along lines 15—15 of FIG. 14.

In another aspect of the invention, a biosensor 610 is provided in accordance with the present invention. Biosensor 610 is shown in FIGS. 14 and 15 and includes an electrode support substrate 612 that includes first and second surfaces 626, 628 each of which supports an electrical conductor 14 formed as described above with reference to biosensor 10. The conductor 14 is disrupted to define electrodes 616, 618 on the first surface 626 and electrodes 620, 622 on the second surface 628. Biosensor 610 also includes sensor support substrates 630, 632. The substrate 630 extends across electrodes 616, 618 and the substrate 632 extends across the electrodes 620, 622. Biosensor 610 may be formed in a variety of shapes and sizes and from materials similar to biosensor 10 as described above.

Referring to FIG. 15, the electrodes 616, 618 and the electrodes 620, 622 are created or isolated from conductor 14 similar to electrodes 216, 218 as described above with reference to biosensor 210. Electrodes 616, 618 and electrodes 620, 622 each include a contact 644 and a lead 646 extending from the contact 644. See FIG. 14. Contacts 644 are spaced apart from end 32. It is appreciated that the contacts 644 can be formed to have many lengths and can extend to end 32 or to edges 34, 36, or to any number of locations on substrates 630, 632. Likewise, the leads 646 can be formed to have many lengths and extend to a variety of locations on the electrode support substrate 612. It is appreciated that the number of electrodes as well as the spacing between the electrodes may vary in accordance with this disclosure as will be appreciated by one of skill in the art. It is also appreciated that the electrodes 616, 618 and the electrodes 620, 622 may cooperate to form a variety of electrode arrays in accordance with this disclosure.

Sensor support substrates 630, 632 of biosensor 610 each extend to the end 32 of the electrode support substrate 612. It is appreciated, however, the relative positioning between the substrates 630, 632 and the electrode support substrate 612 may vary in accordance with this disclosure. Moreover, the sensor support substrates 630, 632 are formed from materials similar to substrate 22, as described above. As shown in FIG. 15, the sensor support substrate 630 is formed to expose the contacts 644 of the electrodes 616, 618 for engagement with meter contacts 126. Likewise, the sensor support substrate 632 is formed to expose the contacts 644 of the electrodes 620, 622 for engagement with meter contacts 126.

The support substrates 630, 632 are formed to include discrete windows 648, 650 respectively. Each window 648, 650 extends between first and second surfaces 48, 50 and is spaced-apart from end 54. It is appreciated that at least one of the windows may be used to perform alignment of the sensor support substrate 630 with the electrode support substrate 612 and the sensor support substrate 632 with the electrode support substrate 612. It is also appreciated that at least one window may be used to perform alignment for other manufacturing processes such as dispensing, labeling, cutting, punching, etc. Moreover, it is appreciated that the windows 648, 650 can take on a variety of shapes and sizes as described above with reference to windows 64 in accordance with the present disclosure.

Biosensor 610 is manufactured in a similar manner to biosensor 10, except for the following differences:

First, in the window punch and web slit station 86, two windows 648 are formed in the web of the sensor support substrate. Likewise, either in the station 86, or in a second slit station, two windows 650 are formed in a second web of a sensor support substrate. Second, in process two, a roll of electrode support material that is metallized on first and second surfaces 626, 628 is fed into an ablation/washing and drying station 94. In the ablation station 94, each metallic layer of the metallized film is ablated in a pre-determined pattern, to form a ribbon of support material with isolated electrode patterns on surfaces 626, 628. The energy required for ablation is similar to that described above with reference to biosensor 10.

Next, in process three, the first and second rolls of punched sensor support substrates are fed into a cutting and lamination station 98. At the same time, the ribbon of support material with isolated electrode patterns is fed into the station 98. The thermoplastic resin coated first surface of the sensor support substrates are each applied to the first and second surfaces 626, 628 of the electrode support substrate material so that the windows 648, 650 are in general alignment with the contacts 644. It is appreciated that the windows 648, 650 may in fact be used as a built-in fiducial for alignment the sensor support substrates with the ribbon of support material. Once aligned, the web of sensor support substrates is heat-sealed to the ribbon of support material to form a subassembly.

In process four, the subassembly is fed into a first reagent dispensing station 102. A reagent that has been compounded is fed, as shown by arrow 104, into the dispensing station 102 where it is applied in a liquid form in multiple shots to the array on the first surface 626. The subassembly is then fed into a second reagent dispensing station (not shown) where a second reagent that has been compounded is fed into the dispensing station where it is applied in a liquid form in multiple shots to the array on the second surface 628. It is appreciated that the reagent can be applied in a single shot by a custom fit precision dispensing station available from Fluilogic Systems Oy, Espoo, Findland. Reagent application techniques are as described above with reference to biosensor 10. It is appreciated that reagents may be applied to the arrays in a liquid or other form and dried or semi-dried onto the arrays in accordance with this disclosure. A reagent-coated subassembly then exits the second station.

In process five, the reagent-coated subassembly is fed into a second cutting and lamination station 108. At the same time, two ribbons of cover material are fed into the station 108. A liner on one side of each ribbon is removed in the station 108. The ribbons of cover material and the subassembly are aligned so that one ribbon of cover material lies across a portion of the electrodes 616, 618 and that the second ribbon of cover material lies across a portion of the electrodes 620, 622 to form an assembled material. The assembled material is cut to form individual biosensors 610 as described above with reference to biosensor 10.

Biosensor 610 is used in a manner similar to biosensor 210. Likewise, cooperation between the biosensor 610 and a meter are similar to that described above with reference to biosensor 10. A meter suitable for use with biosensor 610 will include meter contacts that will become aligned with windows 648, 650 when the biosensor 610 is inserted into the meter.

The processes and products described above include disposable biosensors 10, 210, 310, 410, 510, and 610 especially for use in diagnostic devices. Also included, however, are electrochemical sensors for non-diagnostic uses, such as measuring an analyte in any biological, environmental, or other sample. As discussed above, biosensor 10 can be manufactured in a variety of shapes and sizes and be used to perform a variety of assays, non-limiting examples of which include current, charge, impedance conductance, potential or other electrochemical indicative property of the sample applied to biosensor.

Although the invention has been described in detail with reference to a preferred embodiment, variations and modifications exist within the scope and spirit of the invention, on as described and defined in the following claims.

What is claimed is:

1. A method of forming a biosensor, the method comprising the steps of:

forming electrodes on a first surface of an electrode support substrate, each electrode including a meter-contact portion and a measurement portion, forming a sensor support substrate having opposite ends and at least one window spaced apart from the opposite ends, coupling the sensor support and the electrode support substrate together so that the at least one window is aligned with the meter-contact portion of the electrodes, and applying a reagent to the measurement portion of the electrodes, wherein a greater number of windows are formed on the electrode support substrate as are electrodes formed on the electrode support substrate.

2. The method of claim 1 further comprising the step of forming electrodes on a second surface of the electrode support substrate.

3. The method of claim 2 further comprising the steps of forming a second sensor support substrate and coupling the second sensor support substrate to the second surface of the electrode support substrate.

4. The method of claim 1 wherein the electrodes are formed on the electrode support substrate with a laser.

5. The method of claim 1 further comprising forming an opening in the sensor support substrate and the coupling step includes aligning the opening with the measurement portion of the electrodes.

* * * * *